US009273255B2

(12) United States Patent
Heraud et al.

(10) Patent No.: US 9,273,255 B2
(45) Date of Patent: Mar. 1, 2016

(54) PRODUCTION OF MIDDLE DISTILLATES FROM AN EFFLUENT ORIGINATING FROM FISCHER-TROPSCH SYNTHESIS COMPRISING A STEP OF REDUCING THE CONTENT OF OXYGENATED COMPOUNDS

(71) Applicants: ENI S.p.A., Rome (IT); IFP Energies nouvelles, Rueil-Malmaison Cedex (FR)

(72) Inventors: Jean-Philippe Heraud, Saint Pierre De Chandieu (FR); Aline Grezaud, Lyons (FR); Hugues Dulot, Lyons (FR); Christophe Bouchy, Lyons (FR); Vincenzo Calemma, Milan (IT)

(73) Assignees: ENI S.P.A., Rome (IT); IFP ENERGIES NOUVELLES, Rueil-Malmaison Cedex (FR)

( * ) Notice: Subject to any disclaimer, the term of this patent is extended or adjusted under 35 U.S.C. 154(b) by 364 days.

(21) Appl. No.: 13/859,789

(22) Filed: Apr. 10, 2013

(65) Prior Publication Data
US 2013/0270153 A1    Oct. 17, 2013

(30) Foreign Application Priority Data
Apr. 12, 2012    (FR) ...................................... 1201076

(51) Int. Cl.
*C10G 65/12*    (2006.01)
*C07C 5/02*    (2006.01)
(Continued)

(52) U.S. Cl.
CPC ................. *C10G 65/12* (2013.01); *B01J 21/12* (2013.01); *B01J 23/462* (2013.01); *B01J 23/464* (2013.01); *B01J 23/755* (2013.01); *B01J 23/882* (2013.01); *B01J 23/883* (2013.01); *B01J 23/888* (2013.01); *B01J 23/8885* (2013.01); *B01J 35/0026* (2013.01); *B01J 35/0066* (2013.01);
(Continued)

(58) Field of Classification Search
CPC .............. C10G 3/00; C10G 3/42; C10G 3/44; C10G 3/45; C10G 3/46; C10G 45/00; C10G 45/02; C10G 65/02; C10G 65/12; C07C 27/06; C07C 27/08
See application file for complete search history.

(56) References Cited

U.S. PATENT DOCUMENTS 6,583,186 B2    6/2003    Moore, Jr.
6,900,366 B2    5/2005    Rosenbaum et al.
(Continued)

OTHER PUBLICATIONS
IPRP and Written Opinion from FR1201076 dated Oct. 30,2012.
(Continued)

*Primary Examiner* — Brian McCaig
(74) *Attorney, Agent, or Firm* — Millen, White, Zelano & Branigan, P.C.

(57) ABSTRACT

Production of middle distillates from a feedstock produced by Fischer-Tropsch synthesis and containing oxygenated compounds:
a) catalytic hydrotreating; b) hydroisomerization/hydrocracking at least a part of liquid and gaseous effluent originating from a); c) gas/liquid separation of the stream from b) into a gaseous fraction comprising predominantly hydrogen, a hydroisomerized/hydrocracked organic liquid fraction and an aqueous fraction; d) fractionation of the organic liquid fraction in c) to obtain at least one fraction of middle distillates; and e) catalytic methanation of CO and $CO_2$ on at least a part of said gaseous fraction in c) before hydrotreating a), and/or on at least a part of the liquid and gaseous effluent originating from a) in which the hydrogen in a) is obtained at least partly from the gaseous fraction separated in c).

15 Claims, 3 Drawing Sheets

(51) Int. Cl.

| | |
|---|---|
| *C07C 1/04* | (2006.01) |
| *C07C 1/12* | (2006.01) |
| *B01J 21/12* | (2006.01) |
| *B01J 23/46* | (2006.01) |
| *B01J 23/755* | (2006.01) |
| *B01J 23/882* | (2006.01) |
| *B01J 23/883* | (2006.01) |
| *B01J 23/888* | (2006.01) |
| *B01J 35/00* | (2006.01) |
| *B01J 35/10* | (2006.01) |
| *B01J 37/00* | (2006.01) |
| *B01J 37/02* | (2006.01) |
| *C10G 65/02* | (2006.01) |
| *C07C 27/06* | (2006.01) |
| *C07C 27/08* | (2006.01) |
| *C10G 45/00* | (2006.01) |
| *C10G 45/02* | (2006.01) |

(52) U.S. Cl.
CPC .......... B01J 35/1019 (2013.01); B01J 35/1042 (2013.01); B01J 35/1061 (2013.01); B01J 37/0009 (2013.01); B01J 37/0201 (2013.01); C07C 1/0465 (2013.01); C07C 1/12 (2013.01); C07C 5/02 (2013.01)

(56) References Cited

U.S. PATENT DOCUMENTS

| | | | |
|---|---|---|---|
| 8,137,531 | B2 | 3/2012 | Farshid et al. |
| 2002/0128331 | A1 | 9/2002 | Rosenbaum et al. |
| 2002/0144929 | A1 | 10/2002 | Moore, Jr. et al. |
| 2003/0057135 | A1* | 3/2003 | Benazzi et al. ................. 208/57 |
| 2003/0080027 | A1 | 5/2003 | Rosenbaum et al. |
| 2005/0092653 | A1 | 5/2005 | Farshid et al. |
| 2009/0018374 | A1 | 1/2009 | Bijlsma et al. |
| 2012/0004329 | A1* | 1/2012 | Iwama .......................... 518/700 |
| 2012/0029095 | A1 | 2/2012 | Junaedi et al. |
| 2013/0105358 | A1* | 5/2013 | Bouchy ............... C10G 65/043 208/57 |

OTHER PUBLICATIONS

Arno de Klerk "Hydroprocessing peculiarities of Fischer-Tropsch syncrude" ScienceDirect, Elsevier, Catalysis Today 130, [2008] pp. 439-445.

Kriston P. Brooks, et al. "Methanation of carbon dioxide by hydrogen reduction using the Sabatier process in microchannel reactors" Elsevier, Chemical Engineering Science 62 [2007] pp. 1161-1170.

C. Bouchy et al. "Fischer-Tropsch Waxes Upgrading via Hydrocracking and Selective Hydroisomerization" Oil and Gas Science and Technology Rev. IFP, vol. 64, No. 1 [2009] pp. 91-112.

\* cited by examiner

PRODUCTION OF MIDDLE DISTILLATES FROM AN EFFLUENT ORIGINATING FROM FISCHER-TROPSCH SYNTHESIS COMPRISING A STEP OF REDUCING THE CONTENT OF OXYGENATED COMPOUNDS

This application claims the benefit of priority to French Patent Application No. 1201076, filed on Apr. 12, 2012, and is incorporated herein by reference in its entirety.

The present invention relates to a method for producing middle distillates from a feedstock produced by Fischer-Tropsch synthesis and containing oxygenated compounds.

PRIOR ART

In the low-temperature Fischer-Tropsch process, synthesis gas ($CO+H_2$) is converted catalytically into water and into a hydrocarbon effluent comprising unsaturated compounds, oxygenated compounds and essentially linear paraffinic hydrocarbons in gaseous, liquid or solid form. Said effluent thus produced is generally free from heteroatomic impurities such as, for example, sulphur, nitrogen or metals. Said paraffinic feedstock also contains hardly any or no aromatics, naphthenes and more generally ring compounds.

The liquid hydrocarbons produced by Fischer-Tropsch synthesis cannot be incorporated directly in the fuel pools or used as lubricants. As an example, the melting point of a paraffin with 20 carbon atoms and having a boiling point of 340° C. is about 37° C., which makes its direct incorporation in the gas oil cut impossible in view of the required specification of −15° C. Moreover, these liquid hydrocarbons are composed predominantly of paraffins, but also contain olefins and oxygenated compounds. These liquid hydrocarbons thus need to be converted into higher-grade products, such as for example kerosene and gas oil, which are obtained, for example, after catalytic reactions of hydroisomerization and hydrocracking.

All the catalysts currently used in hydroisomerization/hydrocracking are of the bifunctional type, combining an acid function with a hydrogenating function. The acid function is supplied by supports with large surface areas (generally 150 to 800 $m^2 \cdot g^{-1}$) displaying Brønsted acidity, such as halogenated aluminas (in particular chlorinated or fluorinated), phosphorus-containing aluminas, combinations of oxides of boron and aluminium, silica-aluminas or zeolites. The hydrogenating function is supplied either by one or more metals of group VIII of the periodic table, such as iron, cobalt, nickel, ruthenium, rhodium, palladium, osmium, iridium and platinum, or by a combination of at least one group VI metal such as chromium, molybdenum and tungsten and at least one group VIII metal.

The balance between the two functions—acid and hydrogenating—is one of the parameters governing the activity and selectivity of the catalyst. A weak acid function and a strong hydrogenating function produce catalysts with low activity and selectivity for isomerization whereas a strong acid function and a weak hydrogenating function produce catalysts that are very active and selective for cracking. A third possibility is to use a strong acid function and a strong hydrogenating function in order to obtain a catalyst that is very active but also very selective for isomerization. It is therefore possible, by judicious selection of each of the functions, to adjust the activity/selectivity combination of the catalyst.

It is known, in the area of hydrocracking and hydroisomerization of paraffinic feedstocks originating from Fischer-Tropsch synthesis, that the presence of oxygenated compounds in the paraffinic feedstocks originating from Fischer-Tropsch synthesis can affect the balance between the acid and hydrogenating functions of the downstream hydrocracking/hydroisomerization catalyst and therefore affect its catalytic properties. The oxygenated compounds present in said paraffinic feedstocks are generally oxides of carbon such as carbon monoxide and carbon dioxide (CO and $CO_2$), water or else alcohols and/or carboxylic acids, esters and ketones.

For example, D. Leckel in D. Leckel, Energy & Fuels 2005, 19, 1795-1803 reports a study showing that removing oxygenated compounds by hydrotreating a feedstock originating from Fischer-Tropsch synthesis makes it possible to improve the activity of the downstream hydrocracking catalyst by about fifteen degrees Celsius, but impairs the selectivity of the catalyst for production of middle distillates. Now, during the step of hydrotreating the paraffinic feedstock the hydrocarbon compounds having at least one double bond are hydrogenated, whereas the oxygenated compounds such as the alcohols and/or carboxylic acids, esters and ketones are decomposed. This hydrotreating step has low conversion. The decomposition products in this step are paraffins obtained from the olefinic compounds and water, CO and $CO_2$ obtained from the decomposition of the alcohols and/or carboxylic acids, esters and ketones. Thus, as the cycles proceed, CO and $CO_2$ become more and more concentrated in the recycled hydrogen, and consequently in the hydrotreating unit, and then in the effluent leaving said hydrotreating unit, and consequently greatly inhibit the catalysts used downstream, in particular the hydroisomerization/hydrocracking catalyst.

Several solutions have been proposed in the prior art for limiting the content of oxygenated compounds present in the hydrogen entering the hydroisomerization/hydrocracking units.

Thus, patent EP 0 583 836 B2 teaches the use of a method for preparing gas oil implementing: a) a step of hydrotreating the hydrocarbon feedstock originating from Fischer-Tropsch synthesis in order to saturate the olefins in the feedstock and decompose the oxygenated compounds present, followed by a step (b) of removal of the $C_4^-$ fraction from the hydrotreated feedstock and a step c) of hydrocracking of at least a part of the hydrocarbon effluent from step b). It is taught that the implementation of steps (a) and (b) makes it possible to prolong the life of the hydroconversion catalyst in step (c) as well as improve the selectivity of the catalyst for production of gas oil.

U.S. Pat. No. 6,709,569 B2 describes a specific method for production of hydrocarbon effluent of the middle distillate type from a feedstock originating from a Fischer-Tropsch synthesis process, said feedstock being fractionated into a light fraction and a heavy fraction, so that said light fraction undergoes a step of removal of the oxides of carbon dissolved in said light fraction ($C_3$-$C_{20}$ fraction) by stripping, distillation or fractionation before undergoing a step of hydrotreating and hydrocracking in a mixture with said heavy fraction.

The applicant, in his previous research, discovered a method for producing middle distillates from a paraffinic feedstock produced by Fischer-Tropsch synthesis comprising at least: a) a step of hydrotreating said feedstock in the presence of hydrogen and a hydrotreating catalyst, b) a step of separation of at least a part of the effluent originating from step a) into at least one light fraction, at least one liquid hydrocarbon effluent and at least one liquid effluent comprising water, c) a step of hydroisomerization/hydrocracking of at least a part of the liquid hydrocarbon effluent originating from step b), in the presence of a hydroisomerization/hydrocracking catalyst and a hydrogen stream that has undergone a purification step in the case when the content of atomic oxygen in said hydrogen stream is greater than 500 ppm by volume, d) a step of fractionation of the effluent from step c) in order to obtain at least one middle distillate fraction.

Therefore there is still a need to provide methods that are more economical and more powerful for treating a feedstock produced by Fischer-Tropsch synthesis in which the downstream hydroisomerization/hydrocracking step takes place in the presence of a feedstock or feedstock stream comprising a limited content of oxygenated compounds, such a limitation making it possible to improve the performance of the hydroisomerization/hydrocracking catalyst but also the low-temperature properties of the middle distillate cut and in particular of the gas oil cut produced by the method, while maintaining a good cetane number.

The applicant has discovered a novel method for producing middle distillates employing a feedstock produced by Fischer-Tropsch synthesis, which undergoes: a) a step of hydrotreating in the presence of hydrogen and of a hydrotreating catalyst under defined operating conditions, b) a step of hydroisomerization/hydrocracking of at least a part of the liquid and gaseous effluent from step a), in the presence of a hydroisomerization/hydrocracking catalyst, c) a step of gas/liquid separation of the stream originating from step b) into a gaseous fraction comprising predominantly hydrogen, a hydroisomerized/hydrocracked organic liquid fraction and an aqueous fraction, d) a step of fractionation of the organic liquid fraction separated in step c) in order to obtain at least one middle distillate fraction, e) a step of methanation of the CO and $CO_2$ in the presence of a methanation catalyst carried out on at least a part of said gaseous fraction separated in step c) before the hydrotreating step a), and/or carried out on at least a part of the liquid and gaseous effluent from the hydrotreating step a), in which method, when the methanation step e) is implemented between step a) and step b), the hydroisomerization/hydrocracking step b) is carried out on at least a part of the gaseous and liquid effluent originating from said step e) and in which the hydrogen in step a) is obtained at least partly from the gaseous fraction separated in step c).

SUBJECT MATTER OF THE INVENTION

The present invention relates to a method for producing middle distillates from a feedstock produced by Fischer-Tropsch synthesis and containing oxygenated compounds, said method comprising at least:

a) a step of hydrotreating in the presence of a hydrotreating catalyst at a temperature comprised between 100 and 450° C., at a pressure comprised between 0.2 and 15 MPa, the hydrogen necessary for the hydrotreating reaction being introduced in said hydrotreating step at a flow rate such that the hydrogen/feedstock volume ratio is comprised between 10 and 3000 normal liters per liter, and at an hourly space velocity comprised between 0.1 and 40 $h^{-1}$, b) a step of hydroisomerization/hydrocracking of at least a part of the liquid and gaseous effluent originating from step a), in the presence of a hydroisomerization/hydrocracking catalyst, c) a step of gas/liquid separation of the stream from step b) into a gaseous fraction comprising predominantly hydrogen, a hydroisomerized/hydrocracked organic liquid fraction and an aqueous fraction, d) a step of fractionation of the organic liquid fraction separated in step c) in order to obtain at least one gaseous fraction comprising predominantly light gases ($C_1$-$C_4$), a gasoline fraction composed essentially of naphtha, a middle distillate fraction composed essentially of kerosene and gas oil and a residual fraction, e) a step of methanation of the CO and $CO_2$ carried out in the presence of a methanation catalyst on at least a part of said gaseous fraction separated in step c) before the hydrotreating step a), and/or on at least a part of the liquid and gaseous effluent from the hydrotreating step a), in which when the methanation step e) is implemented between step a) and step b), the hydroisomerization/hydrocracking step b) is carried out on at least a part of the gaseous and liquid effluent from said step e), and in which the hydrogen in step a) is obtained at least partly from the gaseous fraction separated in step c).

Advantageously according to the invention, the methanation step e) is carried out on at least a part of said gaseous fraction separated in step c) having previously been subjected to a step f) of removal of water.

According to the invention, the catalyst used in step a) comprises at least one hydrogenating-dehydrogenating metal selected from the group comprising the metals of group VIB and of group VIII of the periodic table. Advantageously, said step a) is carried out at a temperature comprised between 100 and 450° C., at a pressure comprised between 0.2 and 15 MPa, the hydrogen coming from the separation step c) being introduced into said hydrotreating step at a flow rate such that the hydrogen/feedstock volume ratio is comprised between 10 and 3000 normal liters per liter, and at an hourly space velocity comprised between 0.1 and 40 $h^{-1}$.

Advantageously according to the invention, step b) is carried out at a temperature comprised between 250 and 450° C., at a pressure comprised between 0.2 and 15 MPa, at a space velocity comprised between 0.1 $h^{-1}$ and 10 $h^{-1}$, and at a hydrogen rate comprised between 100 and 2000 normal liters of hydrogen per liter of feedstock.

In one embodiment of the invention, when the methanation step e) is implemented on the liquid and gaseous effluent originating from the hydrotreating step a) said step e) is implemented in the presence of a methanation catalyst at a temperature comprised between 100 and 450° C., at a pressure comprised between 0.2 and 15 MPa, at a space velocity comprised between 0.1 and 40 $h^{-1}$, with a hydrogen flow rate such that the hydrogen/feedstock volume ratio is comprised between 10 and 3000 normal liters per liter. In such a case, the catalyst used advantageously comprises at least one group VIII non-noble metal selected from nickel and cobalt in combination with at least one group VIB metal selected from molybdenum and tungsten, used alone or in a mixture.

In another embodiment of the invention, when step e) is implemented on the gaseous fraction separated in step c), said step e) is carried out at a temperature comprised between 100 and 600° C., at a pressure comprised between 1 and 10 MPa, and at a hourly space velocity comprised between 20,000 and 80,000 $h^{-1}$. In such a case, the catalyst used advantageously comprises at least one group VIII metal selected from ruthenium, rhodium and nickel.

Advantageously, the catalyst used in step e) is used in reduced form.

Advantageously according to the invention, at least one of the middle distillate fractions composed essentially of kerosene and gas oil and the residual fraction originating from the fractionation step d) are recycled, at least partly, to step a) and/or to step b).

Hereinafter, by "oxygenated molecules, products or compounds" is meant any compound containing at least one oxygen atom such as the alcohols and/or carboxylic acids, esters, ketones etc. The decomposition products of said oxygenated compounds are understood as comprising essentially CO, $CO_2$ and $H_2O$.

BRIEF DESCRIPTION OF THE FIGURES

FIGS. 1 to 3 show diagrams for the implementation of the method according to the invention.

DETAILED DESCRIPTION OF THE INVENTION

The present invention relates to a method for producing middle distillates from a feedstock produced by Fischer-Tropsch synthesis and containing oxygenated compounds, said method comprising at least:
a) a step of hydrotreating in the presence of a hydrotreating catalyst at a temperature comprised between 100 and 450° C., at a pressure comprised between 0.2 and 15 MPa, the hydrogen necessary for the reaction of hydrotreating being introduced in said hydrotreating step at a flow rate such that the hydrogen/feedstock volume ratio is comprised between 10 and 3000 normal liters per liter, and at a hourly space velocity comprised between 0.1 and 40 $h^{-1}$,
b) a step of hydroisomerization/hydrocracking of at least a part of the liquid and gaseous effluent originating from step a), in the presence of a hydroisomerization/hydrocracking catalyst,
c) a step of gas/liquid separation of the stream originating from step b) into a gaseous fraction comprising predominantly hydrogen, a hydroisomerized/hydrocracked organic liquid fraction and an aqueous fraction,
d) a step of fractionation of the organic liquid fraction separated in step c) in order to obtain at least one gaseous fraction comprising predominantly light gases ($C_1$-$C_4$), a gasoline fraction composed essentially of naphtha, a middle distillate fraction composed essentially of kerosene and gas oil and a residual fraction,
e) a step of methanation of the CO and $CO_2$ carried out in the presence of a methanation catalyst
  on at least a part of said gaseous fraction separated in step c) before the hydrotreating step a),
  and/or on at least a part of the liquid and gaseous effluent from the hydrotreating step a), in which when the methanation step e) is implemented between step a) and step b), the hydroisomerization/hydrocracking step b) is carried out on at least a part of the gaseous and liquid effluent from said step e), and in which the hydrogen in step a) is obtained at least partly from the gaseous fraction separated in step c).

Feedstock of the Invention

According to the invention, the feedstock used is a feedstock produced by Fischer-Tropsch synthesis according to methods known to a person skilled in the art. The feedstock according to the invention can comprise oxygenated compounds and essentially linear hydrocarbons in gaseous, liquid or solid form. The synthesis gas (CO+$H_2$) used in Fischer-Tropsch synthesis giving rise to the feedstock according to the invention is advantageously produced from natural gas, charcoal, biomass or from any source of hydrocarbon compounds or from a mixture of these sources.

Preferably, the feedstock according to the invention comprises predominantly n-paraffins. Said feedstock can advantageously comprise a content of n-paraffins greater than 60% by weight relative to the total weight of said feedstock, a content of oxygenated compounds preferably less than 10% by weight, a content of unsaturated compounds, i.e. preferably of olefinic products, preferably less than 20% by weight and a content of iso-paraffins preferably less than 10% by weight relative to the total weight of said feedstock. More preferably, said feedstock comprises a content of n-paraffins greater than 70% by weight and even more preferably greater than 80% by weight relative to the total weight of said feedstock.

Advantageously, said feedstock according to the invention is free from heteroatomic impurities such as, for example, sulphur, nitrogen or metals.

Step a) of Hydrotreating

According to step a) of the method according to the invention, the feedstock according to the invention undergoes a step of hydrotreating in the presence of hydrogen and a hydrotreating catalyst, under defined operating conditions.

According to the invention, the hydrogen used in step a) is at least partly the hydrogen from the gaseous fraction separated in step c) (which may or may not have undergone a methanation step e) and optionally a step f) of removal of water). In the case when the gaseous fraction is subjected to step f), said step f) of removal of water is advantageously implemented before the methanation step e). Advantageously, the gaseous fraction obtained from step e) of methanation of the CO and $CO_2$ can be recycled to step a) of hydrotreating at the same time as fresh hydrogen is supplied.

According to the invention, the gaseous fraction from step c) of gas/liquid separation advantageously comprises between 20 and 99% by volume of hydrogen, preferably comprised between 40 and 99% by volume of hydrogen, more preferably comprised between 50 and 99% by volume of hydrogen, even more preferably comprised between 80 and 99% by volume of hydrogen.

The hydrotreating catalysts used in said step a) are conventional hydrotreating catalysts causing little or no cracking, known to a person skilled in the art. Preferred hydrotreating catalysts are described in patent FR 2 826 972.

Step a) of hydrotreating of the method of the invention is advantageously carried out at a temperature comprised between 100 and 450° C., preferably comprised between 150 and 450° C., more preferably comprised between 150 and 380° C., at a pressure comprised between 0.2 and 15 MPa, preferably comprised between 0.5 and 10 MPa, more preferably comprised between 1 and 9 MPa, even more preferably comprised between 4 and 9 MPa, very preferably comprised between 4 and 8 MPa with a hydrogen flow rate such that the hydrogen/feedstock volume ratio is comprised between 10 and 3000 normal liters per liter, preferably comprised between 20 and 2000 normal liters per liter, more preferably comprised between 30 and 2000 normal liters per liter, very preferably comprised between 30 and 1500 normal liters per liter and at an hourly space velocity, defined as the ratio of the flow rate of the feedstock at ambient temperature and pressure to the volume of catalyst, comprised between 0.1 and 40 $h^{-1}$, preferably comprised between 0.2 and 30 $h^{-1}$, more preferably comprised between 0.2 and 20 $h^{-1}$ and even more preferably comprised between 0.5 $h^{-1}$ and 10 $h^{-1}$.

Said step a) of hydrotreating has the aim of reducing the content of olefinic and unsaturated compounds as well as decomposing the oxygenated compounds, in particular the alcohols and the acids present in said feedstock to CO, $CO_2$ and $H_2O$. This step of hydrotreating is non-converting, i.e. the operating conditions are fixed so that the conversion of the 370° C.$^+$ fraction to 370° C.$^-$ fraction is preferably less than 20% by weight, more preferably less than 10% by weight and very preferably less than 5% by weight.

Under these conditions and at the end of step a) of hydrotreating according to the invention, the residual contents in the whole of the effluent leaving said step a) are advantageously less than 1% by weight of olefins.

Step b) of Hydroisomerization/Hydrocracking

According to the method of the invention, step b) of hydroisomerization/hydrocracking is carried out either directly on at least a part, preferably on all of the gaseous and liquid effluent from step a) of hydrotreating, or on at least a part, preferably on all of the gaseous and liquid effluent from step e) when said step e) is implemented between step a) and step b) of the method, i.e. after step a) and before step b). Step b) is carried out by bringing said effluent into contact with a hydroisomerization/hydrocracking catalyst.

Advantageously, step b) of hydroisomerization/hydrocracking is carried out at a temperature comprised between 250 and 450° C., preferably between 280° C. and 450° C., more preferably between 300 and 450° C., and even more preferably between 320 and 420° C., at a pressure comprised between 0.2 and 15 MPa, preferably between 0.5 and 10 MPa, more preferably between 1 and 9 MPa, at a space velocity defined as the ratio of the flow rate of the feedstock at ambient temperature and pressure to the volume of catalyst comprised between $0.1\ h^{-1}$ and $10\ h^{-1}$, preferably between $0.2$ and $7\ h^{-1}$, more preferably between $0.5$ and $5\ h^{-1}$, at a hydrogen rate comprised between 100 and 2000 normal liters of hydrogen per liter of feedstock per hour and preferably between 150 and 1500 normal liters of hydrogen per liter of feedstock and more preferably between 300 and 1500 normal liters of hydrogen per liter of feedstock.

According to the method of the invention, the hydroisomerization/hydrocracking catalyst used in step b) advantageously comprises at least one hydrogenating-dehydrogenating metal selected from the group comprising the metals of group VIB and of group VIII of the periodic table and at least one Brønsted solid acid, i.e. a solid that can release one or more protons, and optionally a binder. Preferably, said hydroisomerization/hydrocracking catalyst comprises either at least one group VIII noble metal selected from platinum and palladium, used alone or in a mixture, active in their reduced form, or at least one group VIII non-noble metal selected from nickel and cobalt in combination with at least one group VIB metal selected from molybdenum and tungsten, used alone or in a mixture, and preferably used in their sulphided form.

In the case when said hydroisomerization/hydrocracking catalyst comprises at least one group VIII noble metal, the noble metal content of said catalyst is advantageously between 0.01 and 5% by weight relative to the final catalyst, preferably between 0.05 and 4% by weight and very preferably between 0.10 and 2% by weight.

In the case when said hydroisomerization/hydrocracking catalyst comprises at least one group VIB metal in combination with at least one group VIII base metal selected from nickel and cobalt, the content of group VIB metal in said catalyst is advantageously, in oxide equivalent, between 5 and 40% by weight relative to the final catalyst, preferably between 10 and 35% by weight and the content of group VIII metal in said catalyst is advantageously, in oxide equivalent, between 0.5 and 10% by weight relative to the final catalyst, preferably between 1 and 8% by weight and very preferably between 1.5 and 6% by weight.

The metallic function is advantageously introduced on the catalyst by any method known to a person skilled in the art, for example co-mixing, dry impregnation or exchange impregnation.

Advantageously, the Brønsted solid acid consists of silica-alumina or zeolite Y.

Optionally, a binder can also be used during the step of forming of the support. A binder is preferably used when the zeolite is used. Said binder is advantageously selected from silica ($SiO_2$), alumina ($Al_2O_3$), clays, titanium dioxide ($TiO_2$), boron oxide ($B_2O_3$) and zirconia ($ZrO_2$) used alone or in a mixture. Preferably, said binder is selected from silica and alumina and even more preferably, said binder is alumina in all of its forms known to a person skilled in the art, for example gamma-alumina.

A preferred hydroisomerization/hydrocracking catalyst according to the invention advantageously comprises at least one noble metal, said noble metal being platinum and a Brønsted solid acid of the silica-alumina type, without any binder. The silica content of the silica-alumina, expressed in percentage by weight, is generally comprised between 1 and 95%, advantageously between 5 and 95% and preferably between 10 and 80% and even more preferably between 20 and 70% and between 22 and 45%. This silica content is measured accurately by means of X-ray fluorescence.

Several preferred catalysts used in step b) of hydroisomerization/hydrocracking of the method according to the invention are described below.

A preferred hydroisomerization/hydrocracking catalyst used in the method according to the invention comprises a particular silica-alumina. Preferably, said catalyst comprises, and preferably essentially consists of 0.05 to 10% by weight and preferably comprised between 0.1 and 5% by weight of at least one group VIII noble metal, preferably selected from platinum and palladium (preferably platinum) deposited on a silica-alumina support, without any binder, containing a quantity of silica ($SiO_2$) between 1 and 95%, expressed in percentage by weight, preferably between 5 and 95%, preferably between 10 and 80% and very preferably between 20 and 70% and even more preferably between 22 and 45%, said catalyst having:

a BET specific surface area from 100 to 500 m$^2$/g, preferably comprised between 200 m$^2$/g and 450 m$^2$/g, and very preferably between 250 m$^2$/g and 450 m$^2$/g, a mean mesopore diameter comprised between 3 and 12 nm, preferably comprised between 3 nm and 11 nm and very preferably between 4 nm and 10.5 nm, a pore volume of pores the diameter of which is comprised between the average diameter as defined above reduced by 3 nm and the average diameter as defined above increased by 3 nm is greater than 40% of the total pore volume, preferably comprised between 50% and 90% of the total pore volume and very preferably comprised between 50% and 70% of the total pore volume, a total pore volume comprised between 0.4 and 1.2 ml/g, preferably comprised between 0.5 and 1.0 ml/g and very preferably comprised between 0.5 and 0.9 ml/g, a content of alkali or alkaline-earth compounds less than 300 ppm by weight and preferably less than 200 ppm by weight.

The average mesopore diameter is defined as being the diameter corresponding to the cancellation of the curve derived from the mercury intrusion volume obtained from the mercury porosity curve for pore diameters comprised between 2 and 50 nm. The average mesopore diameter of the catalyst is advantageously measured from the pore distribution profile obtained by means of a mercury porosimeter.

Preferably, the dispersion of the metal of said preferred catalyst is advantageously comprised between 20% and 100%, preferably between 30% and 100% and very preferably between 40% and 100%. The dispersion, representing the fraction of metal accessible to the reagent relative to the total quantity of metal of the catalyst, is advantageously measured, for example, by $H_2/O_2$ titration or by transmission electron microscopy.

Preferably, the distribution coefficient of the noble metal of said preferred catalyst is greater than 0.1, preferably greater than 0.2 and very preferably greater than 0.4. The distribution of the noble metal represents the distribution of the metal within the grain of the catalyst, it being possible for the metal to be dispersed well or poorly. Thus, it is possible to have the platinum poorly distributed (for example detected in a ring whose thickness is far less than the radius of the grain), but well dispersed, i.e. all the platinum atoms, located in the ring, will be accessible to the reagents. The distribution coefficient of the noble metal can be measured by a Castaing microprobe.

The noble metal salt is advantageously introduced by one of the usual methods used for depositing metal on the surface of a solid. One of the preferred methods is dry impregnation, which consists of introducing the metal salt in a volume of solution that is equal to the pore volume of the solid mass to be impregnated. Before the reduction operation, the catalyst can advantageously undergo calcination, such as for example treatment under dry air at a temperature from 300 to 750° C. and preferably at a temperature equal to 520° C., for 0.25 to 10 hours and preferably for 2 hours.

Another preferred hydroisomerization/hydrocracking catalyst used in the method according to the invention comprises at least one hydrogenating-dehydrogenating element selected from the group formed by the elements of group VIB and of group VIII of the periodic table, from 0.01 to 5.5% by weight of oxide of a doping element selected from phosphorus, boron and silicon and a non-zeolitic support based on silica-alumina containing a quantity greater than 5% by weight and less than or equal to 95% by weight of silica ($SiO_2$), said catalyst having the following characteristics:

a mean mesopore diameter, measured by mercury porosimetry, comprised between 2 and 14 nm, a total pore volume, measured by mercury porosimetry, comprised between 0.1 ml/g and 0.5 ml/g, a total pore volume, measured by nitrogen porosimetry, comprised between 0.1 ml/g and 0.5 ml/g, a BET specific surface area comprised between 100 and 550 $m^2/g$, a pore volume, measured by mercury porosimetry, comprised in the pores of diameter greater than 14 nm, less than 0.1 ml/g, a pore volume, measured by mercury porosimetry, comprised in the pores of diameter greater than 16 nm, less than 0.1 ml/g, a pore volume, measured by mercury porosimetry, comprised in the pores of diameter greater than 20 nm, less than 0.1 ml/g, a pore volume, measured by mercury porosimetry, comprised in the pores of diameter greater than 50 nm, less than 0.1 ml/g, an X-ray diffraction pattern that contains at least the principal lines characteristic of at least one of the transition aluminas in the group comprising the alpha, rho, chi, eta, gamma, kappa, theta and delta aluminas, a tapped bulk density greater than 0.7 g/ml.

Another preferred hydroisomerization/hydrocracking catalyst used in the method according to the invention comprises (and preferably essentially consists of) 0.05 to 10% by weight and preferably 0.1 to 5% by weight of at least one group VIII noble metal, preferably selected from platinum and palladium and preferably said noble metal being platinum, deposited on a silica-alumina support, without any binder, containing a quantity of silica ($SiO_2$) between 1 and 95%, expressed in percentage by weight, preferably between 5 and 95%, preferably between 10 and 80% and very preferably between 20 and 70% and even more preferably between 22 and 45%, said catalyst having:

a BET specific surface area from 150 to 600 $m^2/g$ and preferably comprised between 200 $m^2/g$ and 600 $m^2/g$, a mean mesopore diameter comprised between 3 and 12 nm, preferably comprised between 3 nm and 11 nm and very preferably between 4 nm and 10.5 nm, a pore volume of pores the diameter of which is comprised between the average diameter as defined above reduced by 3 nm and the average diameter as defined above increased by 3 nm is greater than 60% of the total pore volume, preferably greater than 70% of the total pore volume and very preferably greater than 80% of the total pore volume, a total pore volume less than 1 ml/g, preferably comprised between 0.1 and 0.9 ml/g and very preferably between 0.2 and 0.8 ml/g, a content of alkali-metal compounds or alkaline-earth compounds less than 300 ppm by weight and preferably less than 200 ppm by weight.

Preferably, the dispersion of said preferred catalyst used in step b) of the method according to the invention is advantageously comprised between 20% and 100%, preferably between 30% and 100% and very preferably between 40% and 100%.

Preferably, the distribution coefficient of the noble metal of said preferred catalyst used in step b) of the method according to the invention is greater than 0.1, preferably greater than 0.2 and very preferably greater than 0.4. This distribution coefficient is measured by a Castaing microprobe.

Step b) of hydroisomerization and hydrocracking of the method according to the invention is advantageously carried out under conditions such that the conversion of products with boiling points greater than or equal to 370° C. to products having boiling points less than 370° C. is at least 30% by weight, preferably at least 40% by weight and preferably at least 50% by weight so as to maximize the production of middle distillates (kerosene and gas oil).

The conversion is defined as:

Conversion of the 370° C.+ to 370° C.$^-$=[(% by weight of the 370° C.$^-_{effluent}$)–(% by weight of the 370° C.$^-_{feedstock}$)]/[100–(% by weight of the 370° C.$^-_{feedstock}$)], with: –% by weight of the 370° C.$^-_{effluent}$=fraction by weight of compounds having boiling points less than 370° C. in the effluents, –% by weight of the 370° C.$^-_{feedstock}$=fraction by weight of compounds having boiling points less than 370° C. in the hydroisomerization/hydrocracking feedstock.

Step c) of Gas/Liquid Separation of the Stream from Step b)

According to the method of the invention, the hydroisomerized/hydrocracked stream originating from step b) undergoes a step c) of gas/liquid separation into a gaseous fraction comprising hydrogen, an organic liquid fraction and an aqueous fraction. Said separation step c) is advantageously carried out by any method and technique known to a person skilled in the art. Preferably, said step c) is advantageously carried out by distillation, stripping and/or flash, combined with drying, passing over a desiccator or drying agent, or a trapping sieve (of the alumina type), solvent extraction, decanting or by a combination of at least two of these methods. Advantageously, said step c) comprises a flash operation, followed by a decanting operation.

According to a variant of the method of the invention, at least a part, preferably the whole of said gaseous fraction comprising predominantly hydrogen and separated in step c) is advantageously subjected to an optional step f) of removal of water. This step f) is carried out by any methods and techniques known to a person skilled in the art such as drying, passing over a molecular sieve, decanting etc. Advantageously, step f) is carried out on at least a part, preferably the whole of said gaseous fraction after the separation step c) and preferably before the methanation step e).

The aqueous fraction from step c) is generally sent to a water treatment unit.

Step d) of Fractionation of the Organic Liquid Fraction Originating from Step c)

According to step d) of the method according to the invention, the organic liquid fraction originating from step c) undergoes a fractionation step in order to obtain at least a gaseous fraction comprising predominantly light gases ($C_1$-$C_4$), a gasoline fraction composed essentially of naphtha, a middle distillate fraction composed essentially of kerosene and gas oil and a residual fraction.

Advantageously, step d) of the method according to the invention is carried out in a distillation train that incorporates atmospheric distillation and optionally vacuum distillation. Said step d) has the aim of separating the conversion products with boiling point less than 220° C., preferably less than 290° C. and more preferably less than 370° C. and in particular including those formed during step b) of hydroisomerization/hydrocracking. Step d) also makes it possible to separate the residual fraction the initial boiling point of which is generally greater than at least 220° C., preferably greater than 290° C. and preferably greater than or equal to at least 370° C. Among the hydroisomerized conversion products originating from step b), besides the light gases, at least one gasoline (or naphtha) fraction and at least one kerosene and gas oil middle distillate fraction are separated.

Preferably, the residual fraction, whose initial boiling point is generally greater than at least 220° C., preferably greater than or equal to at least 290° C. and even more preferably at least 370° C. is recycled wholly or partly to the hydrotreating step a) or the hydroisomerization/hydrocracking step b) of the method according to the invention. According to another embodiment, said residual fraction can supply excellent bases for oils.

It may also be advantageous to recycle, to step a) and/or to step b), at least partly, at least one of the middle distillate fractions composed essentially of kerosene and gas oil and the residual fraction from the fractionation step d).

The gas oil and kerosene cuts are preferably recovered separately or mixed, but the cut-off points can be adjusted as required.

Step e) of Methanation of CO and $CO_2$

According to the method of the invention, step e) of methanation of CO and $CO_2$ is implemented on at least a part, preferably the whole of said gaseous fraction separated in step c) before it is recycled to the hydrotreating step a), and optionally after the optional step f) of removal of water, and/or on at least a part, preferably the whole of the liquid and gaseous effluent originating from the hydrotreating step a) so as to remove the oxygenated compounds from them, in particular the CO and $CO_2$ contained initially in the feedstock or resulting from decomposition of the oxygenated compounds in step a).

When step e) of methanation of CO and $CO_2$ is implemented after the optional step f) of removal of water, it is advantageously carried out on at least a part, preferably the whole of said gaseous fraction from the optional step f).

The methanation catalyst used in step e) can be any catalyst known to a person skilled in the art that is active in the methanation of CO and $CO_2$ to methane, preferably a catalyst comprising at least one metal selected from the group comprising the metals of group VIB and of group VIII of the periodic table.

Advantageously, when said step e) is implemented on the gaseous fraction separated in step c), the catalyst used in said step e) is a supported catalyst preferably comprising at least one group VIII metal selected from ruthenium, rhodium and nickel. The support of the catalyst used in said step e) is advantageously selected from titanium dioxide, silica, alumina, zinc oxide or caesium oxide, used alone or in a mixture.

Advantageously, when said step e) is implemented on the liquid and gaseous effluent originating from the hydrotreating step a), the catalyst used in said step e) is a supported catalyst preferably comprising at least one group VIII non-noble metal selected from nickel and cobalt in combination with at least one group VIB metal selected from molybdenum and tungsten, used alone or in a mixture. The support of the catalyst used in said step e) is preferably a support based on alumina. Advantageously, the alumina contains a group VIII metal selected from nickel or cobalt, preferably nickel.

In general, the catalyst used in step e) is advantageously used in reduced form.

Advantageously, the content of group VIB metal in the catalyst used in step e) is, in oxide equivalent, comprised between 5 and 40% by weight relative to the final catalyst, preferably between 5 and 20% by weight and the content of group VIII metal in the catalyst is, in oxide equivalent, comprised between 5 and 40% by weight relative to the final catalyst, preferably between 5 and 20% by weight.

The metallic function is advantageously introduced onto the catalyst by any method known to a person skilled in the art, for example co-mixing, dry impregnation or exchange impregnation. The metallic function is deposited on a mineral support, preferably of low acidity.

In general, the catalyst used in step e) advantageously has:
a BET specific surface area from 100 to 300 $m^2/g$, preferably comprised between 100 $m^2/g$ and 250 $m^2/g$,
a mean mesopore diameter comprised between 10 and 20 nm, preferably comprised between 10 nm and 18 nm and very preferably between 12 nm and 16 nm,
a pore volume of pores the diameter of which is comprised between the average diameter as defined above reduced by 3 nm and the average diameter as defined above increased by 3 nm is greater than 40% of the total pore volume, preferably comprised between 50% and 90% of the total pore volume and very preferably comprised between 50% and 70% of the total pore volume,
a total pore volume comprised between 0.1 and 1 ml/g, preferably between 0.2 and 0.8 ml/g and very preferably between 0.3 and 0.6 ml/g.

According to the invention, the average mesopore diameter is defined as the diameter corresponding to the cancellation of the curve derived from the mercury intrusion volume obtained from the mercury porosity curve for pore diameters comprised between 2 and 50 nm. The average mesopore diameter of the catalyst used in step e) is advantageously measured from the pore distribution profile obtained by means of a mercury porosimeter.

According to the invention, the catalyst used in step e) has a dispersion of the metal or metals advantageously comprised between 20% and 100%, preferably between 30% and 100% and more preferably between 40% and 100%. Said dispersion corresponds to the fraction of metal accessible to the reagent relative to the total amount of metal in the catalyst and is measured by any means known to a person skilled in the art, for example by $H_2/O_2$ titration or by transmission electron microscopy.

According to the invention, the catalyst used in step e) is advantageously reduced beforehand. Reduction of the catalyst used in step e) is advantageously carried out under a stream of hydrogen, pure or in a mixture, preferably of pure hydrogen at a hydrogen flow rate comprised between 10 and 2000 normal liters per hour per liter of catalyst, preferably comprised between 300 and 1500 normal liters per hour per liter of catalyst, preferably at a temperature comprised between 100 and 500° C., preferably between 150 and 450° C., for a time between 1 and 100 hours, preferably between 20 and 80 hours.

Advantageously, when said step e) is implemented on the liquid and gaseous effluent from the hydrotreating step a), said step e) is carried out at a temperature comprised between 100 and 450° C., preferably between 250 and 450° C., more preferably between 280 and 400° C., even more preferably between 280 and 380° C., very preferably between 320 and 380° C., at a pressure comprised between 0.2 and 15 MPa, preferably between 0.5 and 10 MPa, more preferably between 1 and 9 MPa, even more preferably between 4 and 9 MPa, very preferably between 4 and 8 MPa with a hydrogen flow rate such that the hydrogen/feedstock volume ratio is comprised between 10 and 3000 normal liters per liter, preferably between 10 and 2000 normal liters per liter, more preferably between 20 and 2000 normal liters per liter, very preferably between 30 and 1500 normal liters per liter, at an hourly space velocity, defined as the ratio of the flow rate of the feedstock at ambient temperature and pressure to the volume of catalyst comprised between 0.1 and 40 $h^{-1}$, preferably between 0.2 and 30 $h^{-1}$, more preferably between 0.2 and 20 $h^{-1}$ and even more preferably between 0.5 $h^{-1}$ and 10 $h^{-1}$.

Advantageously, when said step e) is implemented on the gaseous fraction separated in step c), said step e) is carried out at a temperature comprised between 100 and 600° C., preferably between 200 and 400° C., more preferably between 300 and 400° C., at a pressure comprised between 1 and 10 MPa, at an hourly space velocity between 20 000 and 80 000 $h^{-1}$, preferably between 25 000 and 60 000 $h^{-1}$, more preferably between 30 000 and 40 000 $h^{-1}$.

Advantages of the Invention

Implementation of the catalyst described above in the hydrotreating step a) of the method of the invention offers the advantages:
- of reducing the content of olefinic compounds in the feedstock,
- of converting, essentially to CO and $CO_2$, the oxygenated compounds such as the alcohols and/or carboxylic acids, esters and ketones present in the feedstock according to the invention, to paraffin and CO, $CO_2$ and $H_2O$.

Implementation of step e) according to the invention offers the advantage of reducing the amount of CO and $CO_2$ contained initially in the feedstock or originating from decomposition of the oxygenated compounds during step a) by methanation.

Overall, implementation of the method according to the invention can provide a more economical and more efficient method of treating a feedstock produced by Fischer-Tropsch synthesis. In fact, the hydroisomerization/hydrocracking step downstream of the hydrotreating step takes place in the presence of an initial feedstock comprising a limited, or even zero content of oxygenated compounds, in particular of CO and $CO_2$. This limitation makes it possible to improve the performance of the hydroisomerization/hydrocracking catalyst, but also the low-temperature properties of the middle distillate cut while maintaining a good cetane number.

Figure 1:
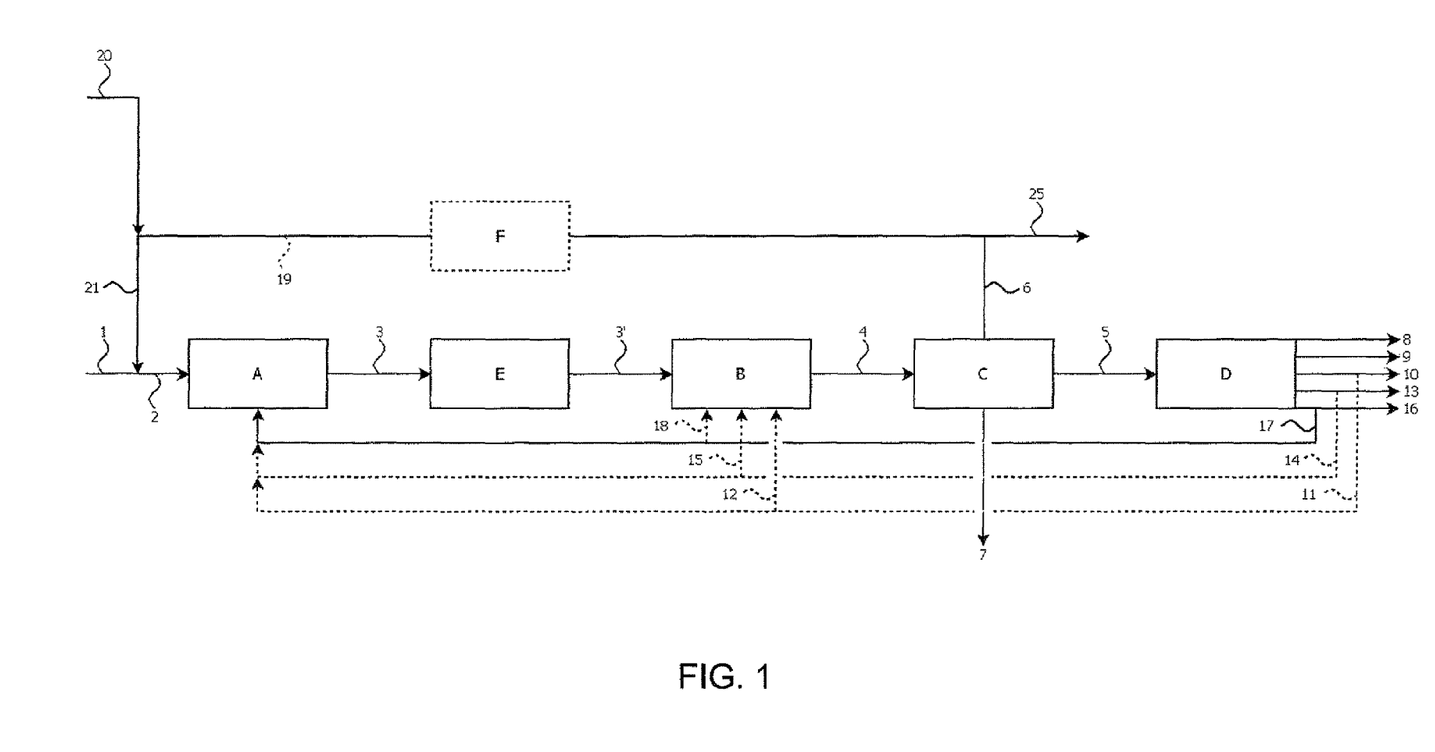
FIG. 1 shows a diagram of the method according to the invention in which the methanation step e) is carried out on at least a part of the liquid and gaseous effluent originating from the hydrotreating step a).

Other advantages, details and features of the invention will become clearer from the description of FIG. 1. FIG. 1 is given by way of example, and is not in any way limitative. This illustration of the method of the invention does not comprise all of the components necessary for its implementation. Only the elements necessary for understanding the invention are represented, as a person skilled in the art is capable of completing this representation for implementing the invention.

DESCRIPTION OF THE DRAWINGS

Figure 2:
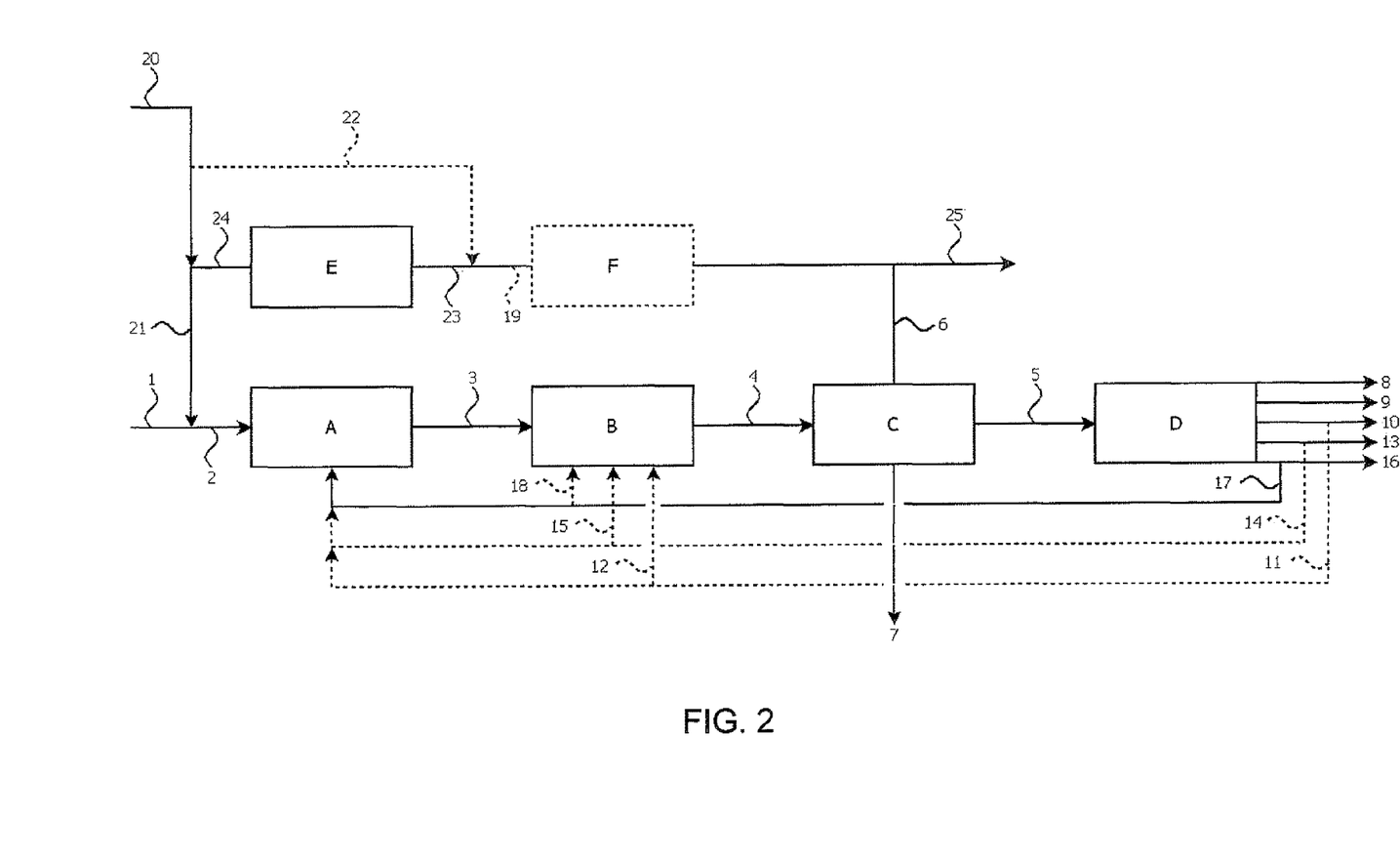
FIG. 2 shows a diagram of the method according to the invention in which the methanation step e) is carried out on at least a part of the gaseous fraction separated in step c) before the hydrotreating step a).
Figure 3:
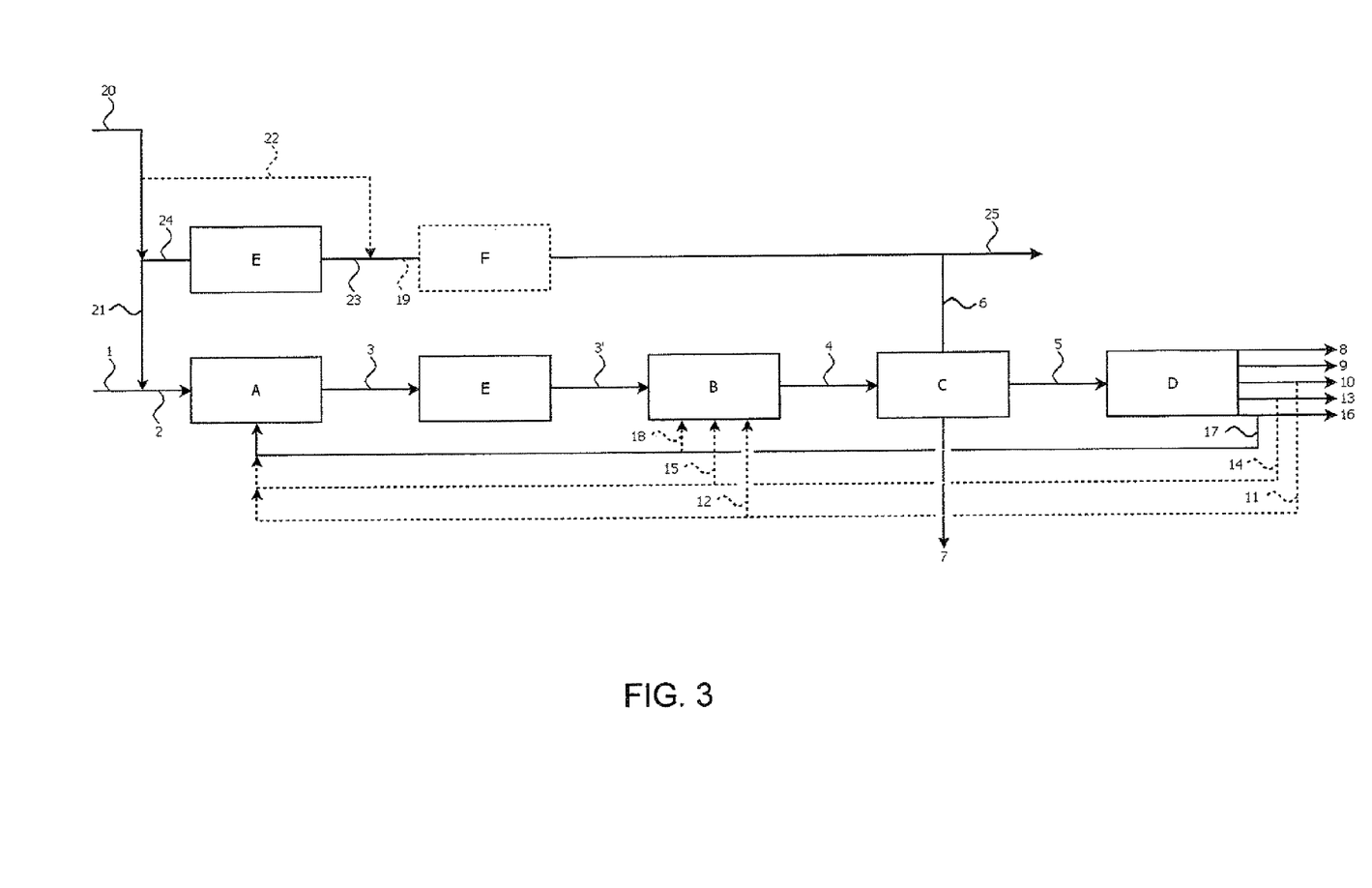
FIG. 3 is a representation of the method according to the invention in which the methanation step e) is carried out simultaneously on at least a part of the liquid and gaseous effluent originating from the hydrotreating step a) and on at least a part of the gaseous fraction separated in step c) before the hydrotreating step a).

FIGS. 1 to 3 show implementations of the general diagram of the method according to the invention.

According to FIG. 1, a feedstock 1 according to the invention is mixed with a hydrogen-rich stream 21 separated in a separation unit C. The mixture thus constituted 2 is fed into a hydrotreating unit A. The liquid and gaseous effluent 3 originating from unit A is sent to unit E for methanation of the CO and $CO_2$. The effluent 3' originating from unit E is sent directly to the hydroisomerization/hydrocracking unit B.

The stream 4 from the hydroisomerization/hydrocracking unit B is separated by means known to a person skilled in the art in the separation unit C into a gaseous fraction 6 rich in hydrogen, an organic liquid fraction 5 and an aqueous fraction 7.

The organic liquid fraction 5 containing normal paraffins and iso-paraffins is sent to a fractionation section D, composed of atmospheric distillation and optionally vacuum distillation, in order to be separated into a gaseous fraction comprising predominantly light gases ($C_1$-$C_4$) 8, a gasoline fraction composed essentially of naphtha 9, a middle distillate fraction composed essentially of kerosene 10, and gas oil 13, and a residual fraction 16. In order to increase the yields of middle distillates, a part of the residual fraction can be recycled upstream of the hydrotreating unit A, stream 17, or of the hydroisomerization/hydrocracking unit, stream 18. A preferred means for improving the low-temperature properties of the gas oil cut is to recycle, in addition to the residual fraction 16, at least a part of the effluent 13 originating from the fractionation section D upstream of the hydrotreating unit A, stream 14, or of the hydroisomerization/hydrocracking unit B, stream 15. Similarly, recycling of at least a part of the kerosene fraction 10 upstream of the hydrotreating unit A, stream 11, or of the hydroisomerization/hydrocracking unit B, stream 12, makes it possible to improve the low-temperature properties of the kerosene cut considerably.

The gaseous fraction 6 from the separation unit C is rich in hydrogen and also contains the oxygenated compounds such as carbon monoxide, carbon dioxide and water, in variable contents.

Optionally, the gaseous fraction 6 passes through a unit for removal of water F in order to reduce the quantity of water.

The gaseous fraction 19 from the optional unit for removal of water F is recycled to the hydrotreating unit A.

If necessary, a supplement of fresh hydrogen 20, pure or obtained from conventional processes such as steam reforming or catalytic reforming, can be injected mixed with the hydrogen 21.

FIG. 2 shows the embodiment according to the invention in which the effluent 3 originating from unit A is sent directly to the hydroisomerization/hydrocracking unit B. According to FIG. 2, the gaseous fraction 19 originating from the optional unit for removal of water F is recycled upstream of the hydrotreating unit A, after passing through the methanation unit E. The gaseous fraction from the methanation unit E corresponds substantially to the hydrogen recycled to the hydrotreating unit A. If necessary, a fresh hydrogen stream 20 can be sent (stream 22) into the methanation unit mixed with the gaseous fraction 19 (stream 23).

FIG. 3 shows the diagram according to the invention implementing/employing both a unit for methanation of the liquid and gaseous effluent originating from the hydrotreating unit 3 and of the gaseous fraction separated in the fractionation unit C.

If necessary, a purge is carried out via stream 25.

EXAMPLES

Example 1

Effect of the Presence of the Oxygen Content in the Hydrogen for the Hydrocracking/Isomerization Step Hydrocracking of a feedstock obtained from Fischer-Tropsch synthesis is carried out on a cobalt catalyst C2. The characteristics of the feedstock are presented in Table 1 below:

TABLE 1

| Characteristics of the feedstock | | |
|---|---|---|
| density at 15° C. | 0.797 | g/cc |
| sulphur | < detection limit | ppmw |
| nitrogen | 7 | ppmw |
| oxygen | 0.3% | by weight |
| n-paraffins | 82% | by weight |
| i-paraffins | 6% | by weight |
| naphthenes | 0% | by weight |
| aromatics | 0% | by weight |
| olefins | 11% | by weight |
| simulated distillation | | |
| 5 | 175° | C. |
| 20 | 228° | C. |
| 50 | 346° | C. |
| 70 | 424° | C. |
| 95 | 570° | C. |
| compounds 370° C.+ | 43% | by weight |

The hydrocracking catalyst C2 is prepared according to the following protocol.
Preparation of the Support The silica-alumina powder is prepared according to the following synthesis protocol. The quantities of orthosilicic acid and of aluminium alcoholate are selected so as to have a composition of 70% by weight $Al_2O_3$ and 30% by weight $SiO_2$ in the final solid.

The powder is dried and brought into contact with a quantity of aqueous solution such that the loss on ignition at 550° C. of the cake obtained is about 60% by weight. This cake is mixed and then extruded. Mixing is carried out in a Z-arm mixer. Extrusion is carried out by passing the paste through a die with openings with a diameter of 1.4 mm. The extrudates thus obtained are dried in a stove at 110° C. and then calcined under a stream of dry air (rate of increase 5° C./min). The calcination temperature is adjusted so as to obtain a specific surface area of 310 m²/g.
Preparation of the Catalyst The silica-alumina extrudates are then subjected to a step of dry impregnation with an aqueous solution of hexachloroplatinic acid $H_2PtCl_6$, left to mature in a soaking drum with water for 24 hours at ambient temperature and then calcined for two hours under dry air in traversed bed at 500° C. (rate of temperature increase 5° C./min). The content by weight of platinum in the final catalyst after calcination is 0.70%.

The characteristics of the catalyst thus prepared are as follows:
  a mean mesopore diameter of 6.5 nm,
  a pore volume of pores the diameter of which is comprised between the average diameter as defined above reduced by 3 nm and the average diameter as defined above increased by 3 nm equal to 60% of the total pore volume,
  a total pore volume of 0.70 ml/g,
  a BET surface area of 310 m²/g,
  a sodium content of 110±13 ppm by weight,
  a dispersion of noble metal of 85%,
  a distribution coefficient of noble metal equal to 0.92.
Hydrocracking Operating Conditions Hydrocracking was carried out in the following conditions:
  hourly space velocity HSV (volume of feedstock/volume of catalyst/hour)=2 h$^{-1}$
  total working pressure: 5 MPa
  hydrogen/feedstock ratio: 300 normal liters/liter
  temperature: 270° C.

In order to measure the effect of the oxygenated compounds on catalyst C2, the hydrogen used originates from a standard mixture obtained from Air Liquide containing:
  700 ppmv (parts per million by volume) of oxygen
  1400 ppmv of oxygen.

Said hydrogen streams do not undergo any purification step.

These results are compared with a test carried out with hydrogen having an oxygen content less than 50 ppmv, conducted under the same operating conditions.

Table 2 presents the distribution, by cut, of the hydrocracked effluent as a function of the oxygen content in the hydrogen.

Analyses by gas chromatography make it possible to obtain the distribution of the various cuts in the hydrocracked effluent (Table 2):
  $C_1$-$C_4$ cut: hydrocarbons with 1 to 4 carbon atoms inclusive
  $C_5$-$C_9$ cut: hydrocarbons with 5 to 9 carbon atoms inclusive (naphtha cut)
  $C_{10}$-$C_{14}$ cut: hydrocarbons with 10 to 14 carbon atoms inclusive (kerosene cut)
  $C_{15}$-$C_{22}$ cut: hydrocarbons with 15 to 22 carbon atoms inclusive (gas oil cut)
  $C_{22+}$ cut: hydrocarbons with more than 22 carbon atoms (370° C.$^+$ cut).

TABLE 2

Distribution, by cuts, of the hydrocracked effluent (GC analysis) as a function of the oxygen content in the hydrogen

| | content of atomic oxygen in the hydrogen, ppmv | | |
|---|---|---|---|
| | <50 | 700 | 1400 |
| $C_1$-$C_4$ cut, % by weight | 2.3 | 2.0 | 1.8 |
| $C_5$-$C_9$ cut, % by weight | 11.6 | 10.2 | 9.2 |
| $C_{10}$-$C_{14}$ cut, % by weight | 31.8 | 30.6 | 30.0 |
| $C_{15}$-$C_{22}$ cut, % by weight | 41.7 | 40.8 | 40.5 |
| $C_{22}^+$ cut, % by weight | 12.6 | 16.4 | 18.5 |

Comparison of the results shows that the presence of oxygen in the hydrogen has a negative impact on the performance of the hydrocracking and isomerization catalyst. Thus, the percentage of middle distillates ($C_{10}$-$C_{22}$ cut) present in the hydrocracked effluent is decreased when oxygen is present in the hydrogen since this percentage changes from 73.5% for a content of atomic oxygen less than 50 ppmv to 71.4% for a content equal to 700 ppmv and to 70.5% for a content equal to 1400 ppmv.

Example 2

Treatment of a Feedstock Originating from the Fischer-Tropsch Process not According to the Invention The feedstock treated by the method of the invention is an effluent originating from Fischer-Tropsch synthesis. The feedstock has the following characteristics shown in Table 3:

TABLE 3

Characteristics of the feedstock

| | |
|---|---|
| density at 15° C. | 0.784 g/cc |
| sulphur | 1.3 ppmw |
| nitrogen | 1.4 ppmw |
| oxygen | 0.8% by weight |
| n-paraffins | 77% by weight |
| i-paraffins | 3.5% by weight |
| naphthenes | 0.1% by weight |
| aromatics | 0.0% by weight |
| olefins | 15% by weight |
| simulated distillation | |
| 5 | 120° C. |
| 20 | 196° C. |
| 50 | 318° C. |
| 70 | 400° C. |
| 95 | 547° C. |
| compounds 370° C.+ | 37% by weight |

The operating conditions for hydrotreating are:
a pressure of 6.5 MPa,
a temperature equal to 335° C.,
an hourly space velocity (HSV) equal to 1 h$^{-1}$,
an $H_2$/feedstock ratio of 600 Nl/l In this example, no device for treatment of CO and $CO_2$ is installed in the unit and no recycling of gas is carried out upstream of the hydrotreating unit. The content of CO and $CO_2$ in the gas leaving the hydrotreating unit is 0.4% by volume and 0.18% by volume, respectively. The hydrogen content is 98.79% by volume and the methane content is 0.11% by volume.

Example 3

Treatment of a Feedstock Obtained from the Fischer-Tropsch Process not According to the Invention The feedstock in Example 2 is treated under the same operating conditions as in Example 2.

In this example, no device for treatment of CO and $CO_2$ is installed in the unit. Total gas recycling is carried out upstream of the hydrotreating unit. The composition of the recycled gas is given in Table 4.

TABLE 4

Composition of the recycled gas

| Compounds | Content [% by volume] |
|---|---|
| Hydrogen | 80.1 |
| Carbon monoxide | 15.5 |
| Carbon dioxide | 1.7 |
| Methane | 1.9 |

Example 4

Treatment of a Feedstock Obtained from the Fischer-Tropsch Process According to the Invention The feedstock in Example 2 is treated under the same operating conditions as in Example 2.

In this example, a device for treating CO and $CO_2$ is installed in the unit for the gaseous fraction recycled to the hydrotreating step. Total gas recycling is carried out upstream of the hydrotreating unit. The composition of the recycled gas is given in Table 5.

TABLE 5

Composition of the recycled gas

| Compounds | Content [% by volume] |
|---|---|
| Hydrogen | 87.3 |
| Carbon monoxide | 0 |
| Carbon dioxide | 0 |
| Methane | 11.91 |

Implementation of the method according to the invention, compared with Example 3 (not according to the invention), permits conversion of the CO and $CO_2$ to methane. Relative to Example 3 (not according to the invention), the gas recycled to the hydrotreating unit after treatment contains neither CO, nor $CO_2$ and its methane concentration goes up from 1.9% to 11.91% by volume.

Example 5

Treatment of a Feedstock Obtained from the Fischer-Tropsch Process According to the Invention The feedstock in Example 2 is treated in the same operating conditions as in Example 2.

In this example, a device for treating CO and $CO_2$ is installed in the unit for the liquid and gaseous effluent from the hydrotreating step. Total gas recycling is carried out upstream of the hydrotreating unit. The composition of the gaseous effluent leaving the device for treating CO and $CO_2$ is given in Table 6.

TABLE 6

Composition of the gaseous effluent at the outlet of the device for treating CO and $CO_2$

| Compounds | Content [% by volume] |
|---|---|
| Hydrogen | 87.4 |
| Carbon monoxide | 0 |

TABLE 6-continued

Composition of the gaseous effluent at the outlet of the device for treating CO and $CO_2$

| Compounds | Content [% by volume] |
|---|---|
| Carbon dioxide | 0 |
| Methane | 11.80 |

Implementation of the method according to the invention, compared with Example 3 (not according to the invention), permits conversion of the CO and $CO_2$ to methane. Relative to Example 3 (not according to the invention), the gaseous effluent leaving the treatment device contains neither CO, nor $CO_2$ and its methane concentration goes up from 1.9% to 11.80% by volume.

The invention claimed is:

1. A method for producing middle distillates from a feedstock produced by Fischer-Tropsch synthesis and containing oxygenated compounds, said method comprising at least:
    a) hydrotreating said feedstock in the presence of a hydrotreating catalyst at a temperature of 100 to 450° C., at a pressure of 0.2 to 15 MPa, the hydrogen necessary for the reaction of hydrotreating being introduced in hydrotreating at a flow rate such that the hydrogen/feedstock volume ratio is 10 to 3000 normal liters per liter, and at an hourly space velocity of 0.1 to 40 $h^{-1}$,
    b) hydroisomerizing/hydrocracking of at least a part of a liquid and gaseous effluent originating from a), in the presence of a hydroisomerization/hydrocracking catalyst,
    c) gas/liquid separation of a stream originating from b) into a gaseous fraction comprising predominantly hydrogen, a hydroisomerized/hydrocracked organic liquid fraction and an aqueous fraction,
    d) fractionating of the organic liquid fraction separated in c) to obtain at least a gaseous fraction comprising predominantly light gases ($C_1$-$C_4$), a gasoline fraction comprising naphtha, a middle distillate fraction comprising kerosene and gas oil and a residual fraction,
    e) methanating CO and $CO_2$ carried out in the presence of a methanation catalyst
        on at least a part of said gaseous fraction separated in c) before recycle of hydrogen to the hydrotreating in a),
        and/or on at least a part of the liquid and gaseous effluent originating from the hydrotreating a),
    in which
        if methanation e) is implemented between a) and b), the hydroisomerization/hydrocracking b) is carried out on at least a part of the gaseous and liquid effluent originating from said e),
    and
        hydrogen in a) is obtained at least partly from the gaseous fraction separated in c).
2. The method according to claim 1 in which said methanation e) is subjected beforehand to f) removal of water.

3. The method according to claim 1 in which said feedstock produced by Fischer-Tropsch synthesis comprises a content of n-paraffins greater than 60% by weight relative to the total weight of said feedstock, a content of oxygenated compounds less than 10% by weight, a content of unsaturated compounds less than 20% by weight and a content of iso-paraffins less than 10% by weight relative to the total weight of said feedstock.

4. The method according to claim 1 in which the catalyst used in a) comprises at least one hydrogenating-dehydrogenating metal of group VIB or of group VIII of the periodic table.

5. The method according to claim 1 in which a) is carried out at a temperature of 100 to 450° C., at a pressure of 0.2 to 15 MPa, the recycle hydrogen being fed into said hydrotreating at a flow rate such that the hydrogen/feedstock volume ratio is 10 to 3000 normal liters per liter, and at a hourly space velocity of 0.1 to 40 $h^{-1}$.

6. The method according to claim 1 in which b) is carried out at a temperature of 250 to 450° C., at a pressure of 0.2 to 15 MPa, at a space velocity of 0.1 $h^{-1}$ to 10 $h^{-1}$, and at a hydrogen rate of 100 to 2000 normal liters of hydrogen per liter of feedstock.

7. The method according to claim 1 in which, if e) is implemented on the liquid and gaseous effluent from the hydrotreating a), said e) is implemented in the presence of a methanation catalyst at a temperature of 100 to 450° C., at a pressure of 0.2 to 15 MPa, at a space velocity of 0.1 to 40 $h^{-1}$, with a hydrogen flow rate such that the hydrogen/feedstock volume ratio is comprised between of 10 and to 3000 normal liters per liter.

8. The method according to claim 7 in which the methanation catalyst used comprises at least one group VIII non-noble metal that is nickel or cobalt in combination with at least one group VIB metal that is molybdenum or tungsten, used alone or in a mixture.

9. The method according to claim 1 in which, if e) is implemented on the gaseous fraction separated in c), said e) is carried out at a temperature of 100 to 600° C., at a pressure of 1 to 10 MPa, at an hourly space velocity of 20 000 to 80 000 $h^{-1}$.

10. The method according to claim 9 in which the methanation catalyst used comprises at least one group VIII metal ruthenium, rhodium or nickel.

11. The method according to claim 1 wherein the catalyst used in e) is used in reduced form.

12. The method according to claim 1 in which said gaseous fraction from e) methanation of CO and $CO_2$ is recycled to the hydrotreating a).

13. The method according to claim 1 in which at least one of the middle distillate fractions comprising kerosene and gas oil and the residual fraction originating from the fractionation d) are recycled, at least partly, to a) and/or to b).

14. The method according to claim 1, wherein the gasoline fraction consists essentially of naphtha.

15. The method according to claim 1, wherein the middle distillate fraction consists essentially of kerosene.

* * * * *